(12) United States Patent
Shirota et al.

(10) Patent No.: US 11,006,913 B2
(45) Date of Patent: May 18, 2021

(54) X-RAY IMAGING APPARATUS

(71) Applicant: Shimadzu Corporation, Kyoto (JP)

(72) Inventors: Ken Shirota, Kyoto (JP); Junpei Sakaguchi, Kyoto (JP); Hiroshi Okumura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 83 days.

(21) Appl. No.: 16/681,001

(22) Filed: Nov. 12, 2019

(65) Prior Publication Data

US 2020/0214655 A1  Jul. 9, 2020

(30) Foreign Application Priority Data

Jan. 8, 2019  (JP) .............................. JP2019-001281

(51) Int. Cl.
*A61B 6/00* (2006.01)
(52) U.S. Cl.
CPC .......... *A61B 6/4476* (2013.01); *A61B 6/4452* (2013.01); *A61B 6/547* (2013.01)
(58) Field of Classification Search
CPC .................................................. A61B 6/0487
See application file for complete search history.

(56) References Cited

U.S. PATENT DOCUMENTS 8,755,492 B2 * 6/2014 Lee ...................... A61B 6/4476
378/115
2019/0239835 A1  8/2019  Okuno et al.

FOREIGN PATENT DOCUMENTS

JP  2010-227376 A  10/2010

OTHER PUBLICATIONS

Product information from a website of Canon Medical Systems Corporation. Available at https://jp.medical.canon/products/xray/radrex_drite (This or similar website appears to have been available as of Sep. 21, 2018).

* cited by examiner

*Primary Examiner* — Dani Fox
(74) *Attorney, Agent, or Firm* — Muir Patent Law, PLLC

(57) ABSTRACT

An X-ray imaging apparatus includes an X-ray tube, an X-ray detector, a moving body configured to support at least one of the X-ray tube and the X-ray detector in such a manner that at least the one of the X-ray tube and the X-ray detector is movable in a predetermined direction, a drive configured to provide an amount of assist for moving the moving body in the predetermined direction, and a controller configured or programmed to perform control to change the amount of assist to be provided to the moving body by the drive according to a height position of the moving body when the moving body is manually moved.

7 Claims, 4 Drawing Sheets

X-RAY IMAGING APPARATUS

CROSS-REFERENCE TO RELATED APPLICATIONS

This application claims the benefit of priority to Japanese Patent Application No. 2019-001281 filed on Jan. 8, 2019, the entire contents of this application being hereby incorporated herein by reference.

BACKGROUND OF THE INVENTION

Field of the Invention

The present invention relates to an X-ray imaging apparatus.

Description of the Background Art

Conventionally, an X-ray imaging apparatus is known. Such an X-ray imaging apparatus is disclosed in Japanese Patent Laid-Open No. 2010-227376, for example.

Japanese Patent Laid-Open No. 2010-227376 discloses an X-ray imaging apparatus including a radiation source, radiation detection means, an operation unit that detects a force for manually moving the radiation source, a servomotor that moves the radiation source, and a controller that controls the servomotor. In the X-ray imaging apparatus described in Japanese Patent Laid-Open No. 2010-227376, when the radiation source is manually moved, the controller controls the rotation speed of the servomotor based on the force for manually moving the radiation source so as to perform operation assist (power assist).

In the X-ray imaging apparatus described in Japanese Patent Laid-Open No. 2010-227376, the controller controls the rotation speed of the servomotor based on the force for manually moving the radiation source so as to perform operation assist (power assist). However, when the radiation source is located at a high position, for example, an operator needs to raise his or her hand to operate the radiation source, and thus it is difficult for the operator to apply a force to the operation unit. Therefore, the force applied to the operation unit becomes weak, and thus sufficient assist cannot be obtained. Consequently, when the radiation source is located at the high position, the operator disadvantageously feels heavy to move the radiation source. Therefore, when the radiation source is manually moved, the operability is disadvantageously decreased depending on the height position of the radiation source.

SUMMARY OF THE INVENTION

The present invention is intended to solve the above problem. The present invention aims to provide an X-ray imaging apparatus capable of significantly reducing or preventing a decrease in operability depending on the height position of at least one of an X-ray tube and an X-ray detector when at least one of the X-ray tube and the X-ray detector is manually moved.

An X-ray imaging apparatus according to an aspect of the present invention includes an X-ray tube configured to irradiate a subject with X-rays, an X-ray detector configured to detect the X-rays transmitted through the subject, a moving body configured to support at least one of the X-ray tube and the X-ray detector in such a manner that at least the one of the X-ray tube and the X-ray detector is movable in a predetermined direction, a drive configured to provide an amount of assist for moving the moving body in the predetermined direction, and a controller configured or programmed to perform control to change the amount of assist to be provided to the moving body by the drive according to a height position of the moving body when the moving body is manually moved.

The X-ray imaging apparatus according to this aspect of the present invention includes the controller configured or programmed to perform control to change the amount of assist to be provided to the moving body by the drive according to the height position of the moving body when the moving body is manually moved. Accordingly, for example, the amount of assist is increased when the height position of the moving body is high such that feeling heavy in moving the moving body can be significantly reduced or prevented even when the height position of the moving body is high. Furthermore, for example, the amount of assist is increased when the height position of the moving body is low such that feeling heavy in moving the moving body can be significantly reduced or prevented even when the height position of the moving body is too low so that it is difficult for an operator to apply a force. Consequently, it is possible to significantly reduce or prevent a decrease in operability depending on the height position of at least one of the X-ray tube and the X-ray detector when at least one of the X-ray tube and the X-ray detector is manually moved.

In the X-ray imaging apparatus according to this aspect of the present invention, the controller is preferably configured or programmed to increase the amount of assist provided to the moving body by the drive when the height position of the moving body is equal to or more than a predetermined height upon manual movement of the moving body. Accordingly, when the moving body is at a high position, the amount of assist is increased, and thus even when the moving body is at a high position, the moving body can be easily moved manually.

In the X-ray imaging apparatus according to this aspect of the present invention, the controller is preferably configured or programmed to make the amount of assist provided to the moving body by the drive constant when the height position of the moving body is less than a predetermined height and the moving body is manually moved, and to increase the amount of assist as a height of the moving body increases when the height position of the moving body is equal to or more than the predetermined height and the moving body is manually moved. Accordingly, when the height position of the moving body is at a low position at which it is relatively easy for the operator to apply a force for moving the moving body, a change in the amount of assist can be significantly reduced or prevented. Thus, it is possible to significantly reduce or prevent a variation in operability depending on the height position at the low position at which it is relatively easy for the operator to move the moving body, and thus a decrease in operability can be significantly reduced or prevented.

In the X-ray imaging apparatus according to this aspect of the present invention, the controller is preferably configured or programmed to change the amount of assist in a horizontal direction to be provided to the moving body by the drive according to the height position of the moving body when the moving body is manually moved. Accordingly, it is possible to effectively significantly reduce or prevent a decrease in operability depending on the height position when the operator moves the moving body in the horizontal direction in which a movement distance is larger than that in a vertical direction.

In the X-ray imaging apparatus according to this aspect of the present invention, the drive preferably includes a motor, and the controller is preferably configured or programmed to control a generated torque of the motor so as to change the amount of assist to be provided to the moving body by the drive according to the height position of the moving body when the moving body is manually moved. Accordingly, the torque (drive force) of the motor is controlled such that an operating force can be assisted. Therefore, the operating force is assisted by a direct force (torque), and thus it is possible to perform good power assist with no sense of strangeness. In this respect as well, a decrease in operability can be significantly reduced or prevented.

The X-ray imaging apparatus according to this aspect of the present invention preferably further includes a position detector configured to detect the height position of the moving body, and the controller is preferably configured or programmed to change the amount of assist to be provided to the moving body by the drive based on the height position detected by the position detector when the moving body is manually moved. Accordingly, the amount of assist can be easily changed according to the height position detected by the position detector.

The X-ray imaging apparatus according to this aspect of the present invention preferably further includes a moving mechanism configured to support the moving body in such a manner that the moving body is movable in the predetermined direction, the moving mechanism preferably includes a plurality of rails provided in a horizontal direction, and the controller is preferably configured or programmed to change the amount of assist in the horizontal direction along the plurality of rails to be provided to the moving body by the drive according to the height position of the moving body when the moving body is manually moved. Accordingly, even when the moving body and the moving body support are heavy, the moving body and the moving body support can be moved along the rails of a guide, and thus the operator can easily move the moving body and the moving body support also when manually moving the moving body.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

(Configuration of X-ray Imaging Apparatus)

The overall configuration of an X-ray imaging apparatus 100 according to the embodiment of the present invention is now described with reference to FIG. 1.

Figure 1:
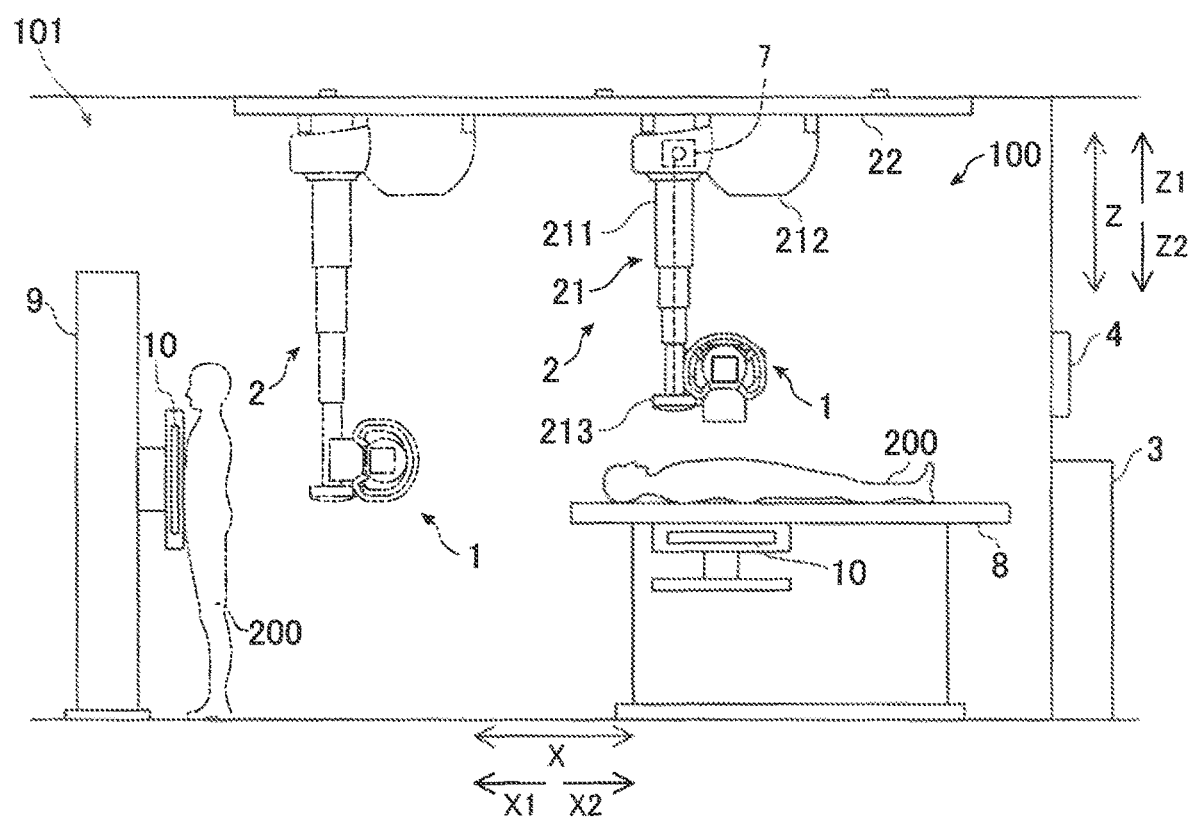
FIG. 1 is a schematic view showing the overall configuration of an X-ray imaging apparatus according to an embodiment of the present invention.

FIG. 1 shows an example of a ceiling-suspended X-ray imaging apparatus 100 installed in an imaging room 101. The X-ray imaging apparatus 100 mainly includes a moving body 1, a moving mechanism 2, a controller 3, a remote control 4, and X-ray detectors 10.

In the ceiling-suspended X-ray imaging apparatus 100, the moving body 1 including an X-ray tube 11 is supported by the moving mechanism 2 so as to be suspended from the ceiling. The moving body 1 is supported by the moving mechanism 2 in such a manner as to be movable in the imaging room 101. Furthermore, the moving mechanism 2 is provided with a position detector 7 that detects the position of the moving body 1.

The X-ray imaging apparatus 100 is a medical X-ray imaging apparatus, and is configured to radiograph a subject 200 to be imaged. The X-ray imaging apparatus 100 includes an imaging table 8 to image the lying subject 200 (in the recumbent position), and an imaging stand 9 to image the standing subject 200 (in the upright position).

The X-ray detectors 10 are movably held by the imaging table 8 and the imaging stand 9, respectively. The X-ray detectors 10 are flat panel detectors (FPDs), for example, and are configured to detect X-rays transmitted through the subject 200. A guide 22 can move the moving body 1 at least between a position at which imaging in the recumbent position using the imaging table 8 is performed (see solid lines in FIG. 1) and a position at which imaging in the upright position using the imaging stand 9 is performed (see two-dot chain lines in FIG. 1).

In imaging in the recumbent position, the moving body 1 is disposed at a position that faces the X-ray detector 10 of the imaging table 8 in a vertical direction, and the subject 200 lying on the imaging table 8 is imaged between the X-ray tube 11 and the X-ray detector 10 that face each other in the vertical direction. In imaging in the upright position, the moving body 1 is disposed at a position that faces the X-ray detector 10 of the imaging stand 9 in a horizontal direction, and the subject 200 standing in front of the imaging stand 9 is imaged between the X-ray tube 11 and the X-ray detector 10 that face each other in the horizontal direction. Furthermore, in the X-ray imaging apparatus 100, general imaging (imaging in which the posture is not specified) in which the subject 200 in an arbitrary posture can be imaged from an arbitrary direction can be performed by disposing a portable X-ray detector 10 at an arbitrary position in the imaging room 101, and moving the moving body 1 to a position that faces the X-ray detector 10.

The X-ray imaging apparatus 100 also includes the controller 3 and the remote control 4. The controller 3 includes a central processing unit (CPU) and a memory. The controller 3 controls X-ray imaging with the X-ray tube 11 and the X-ray detectors 10 and controls movement of the moving body 1. The remote control 4 is provided to perform an operation related to movement of the moving body 1. The remote control 4 has a function of receiving an input operation related to X-ray imaging. The input operation includes auto positioning control, setting of imaging conditions for X-ray imaging, an instruction to start X-ray irradiation, etc.

(Moving Body)

Figure 2:
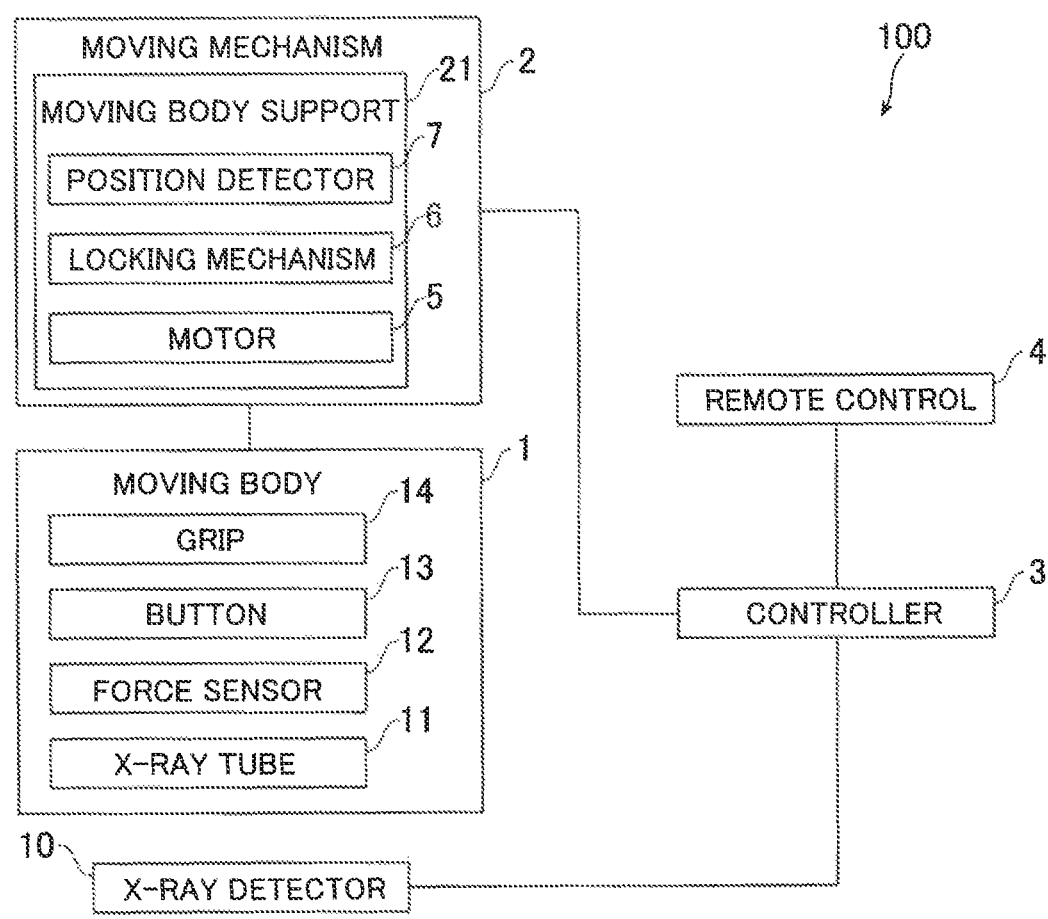
FIG. 2 is a block diagram showing the overall configuration of the X-ray imaging apparatus according to the embodiment of the present invention.
Figure 3:
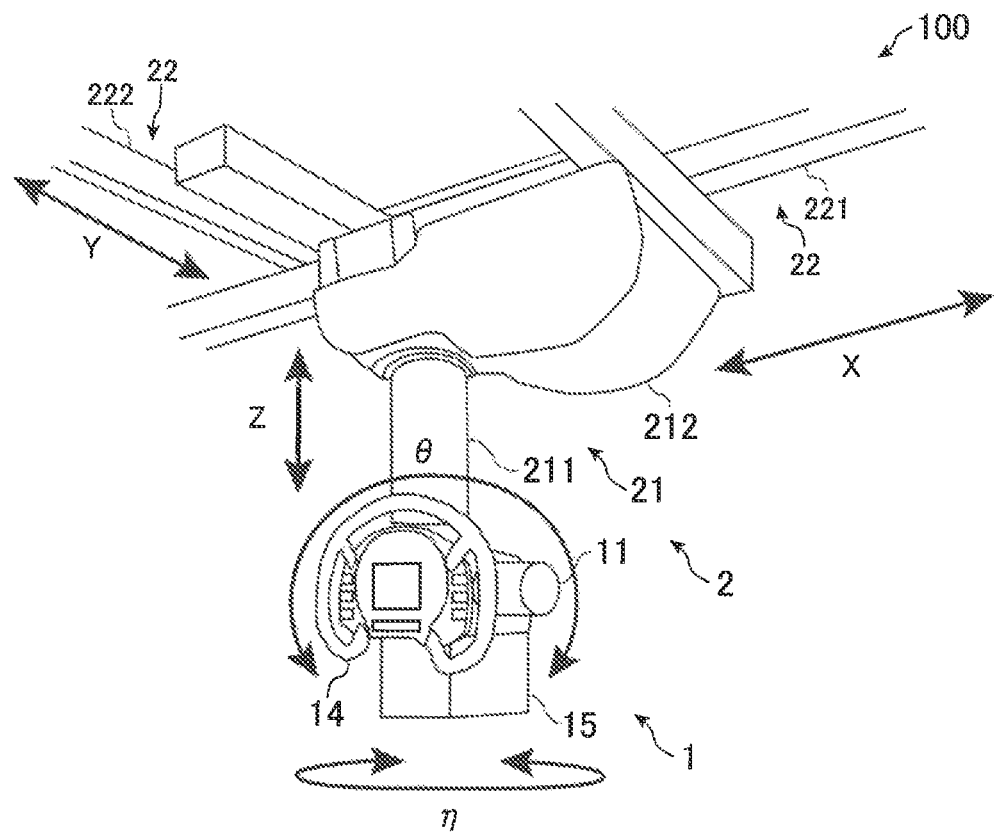
FIG. 3 is a diagram showing the configuration of a moving body and a moving mechanism of the X-ray imaging apparatus according to the embodiment of the present invention.
Figure 4:
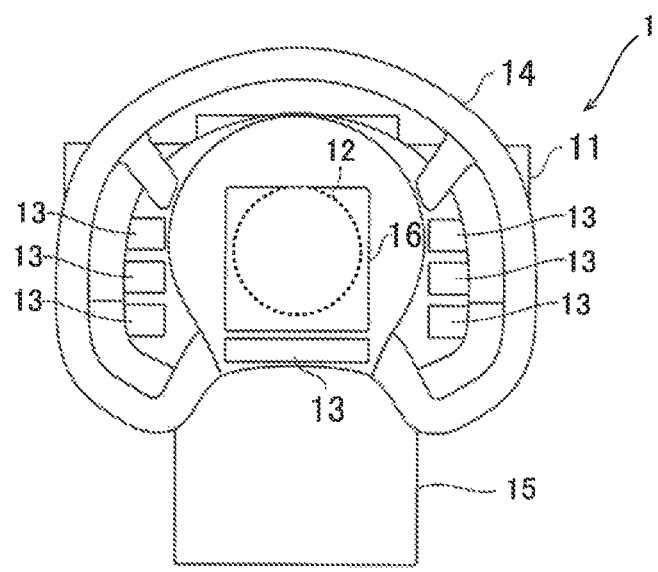
FIG. 4 is a diagram showing the configuration of the moving body of the X-ray imaging apparatus according to the embodiment of the present invention.

As shown in FIGS. 2 to 4, the moving body 1 includes the X-ray tube 11, a force sensor 12, a plurality of buttons 13, a grip 14, a collimator 15, and a touch panel 16. The moving body 1 is configured to be movable in a plurality of directions (predetermined directions) by manual movement or control by the controller 3.

The X-ray tube 11 generates X-rays when a high voltage is applied thereto from a power source (not shown), and irradiates the subject 200 with the X-rays.

The force sensor 12 is disposed in the moving body 1 and can detect a force and a moment applied to the moving body 1 in each direction.

Specifically, the force sensor 12 is configured to detect a force in each of horizontal and vertical translational directions (X, Y, and Z directions) applied in order for an operator to manually move the moving body 1. In addition, the force sensor 12 is configured to detect a moment in each of rotational directions (θ and η directions) about a horizontal axis (R-axis) and a vertical axis (Z-axis) applied to the moving body 1. The force sensor 12 can detect detection direction components of the applied force and moment, and can measure the directions of the force and the moment and the magnitudes of the force and the moment. The detection results of the force sensor 12 are acquired by the controller 3.

The buttons 13 are a plurality of physical buttons disposed on the moving body 1 and pressed by the operator in order to control a locking mechanism 6 (described below), and the plurality of buttons 13 are provided in the vicinity (on the grip 14 or near the grip 14) of the grip 14 of the moving body 1.

The grip 14 is provided on the moving body 1. The grip 14 is held by the operator when the operator manually moves the moving body 1, and transmits an operating force of the operator to the moving body 1.

The collimator 15 includes a plurality of shielding plates (collimator leaves), the positions of which can be adjusted, and has a function of adjusting an X-ray field by partially shielding the X-rays from the X-ray tube 11.

The touch panel 16 is configured to display imaging conditions and a method for X-ray imaging, and can receive input operations from the operator.

(Moving Mechanism)

As shown in FIGS. 1 and 3, the moving mechanism 2 includes a moving body support 21 that supports the moving body 1 in such a manner that the moving body 1 is movable in the plurality of directions (predetermined directions), and the guide 22 including a plurality of rails.

The moving body 1 can be moved by the moving mechanism 2 (the moving body support 21 and the guide 22) in the plurality of directions. As shown in FIGS. 1 and 3, a vertical direction is defined as a Z direction, and two directions orthogonal to each other in the horizontal direction are defined as an X direction and a Y direction.

This embodiment shows an example in which the plurality of directions in which the moving body 1 can be moved by the moving mechanism 2 (the moving body support 21 and the guide 22) include a total of five directions including three translational directions (X, Y, and Z directions), a rotational direction (η direction) about the Z-axis in the vertical direction, and a rotational direction (θ direction) about the R-axis in the horizontal direction, as shown in FIG. 3.

As shown in FIG. 1, the moving body support 21 includes a support rod 211, a base 212, and a rotary holder 213. As shown in FIG. 2, motors 5 are provided corresponding to respective axes inside the moving mechanism 2 (moving body support 21). The motors 5 are examples of a "drive" in the claims.

As shown in FIG. 1, the support rod 211 holds the moving body 1 in such a manner that the moving body 1 can be translated in the vertical direction. The support rod 211 is suspended from the base 212 attached to the guide 22, and is expandable and contractable in the Z direction (vertical direction). With these configurations, the moving body support 21 supports the moving body 1 in such a manner that the moving body 1 is movable in the three translational directions (X, Y, and Z directions). In addition, the rotary holder 213 is provided at the tip (lower end) of the support rod 211.

The rotary holder 213 is supported by the support rod 211 in such a manner as to be rotatable in the η direction about the vertical axis (Z-axis). The Z-axis coincides with the central axis of the support rod 211. One end side of the rotary holder 213 is connected to the support rod 211 and holds the moving body 1 in such a manner that the moving body 1 is rotatable in the θ direction about the horizontal axis (R-axis). The R-axis is the radial direction (horizontal direction) of the support rod 211. With these configurations, the moving body support 21 supports the moving body 1 in such a manner that the moving body 1 is movable in the two rotational directions (η and θ directions).

The rotary holder 213 moves integrally with the moving body 1 in the plurality of directions (X, Y, Z, η, and θ), and thus the operator can move the moving body 1 (X-ray tube 11) in the plurality of directions (X, Y, Z, η, and θ) by holding the grip 14 and applying a force.

Figure 5:
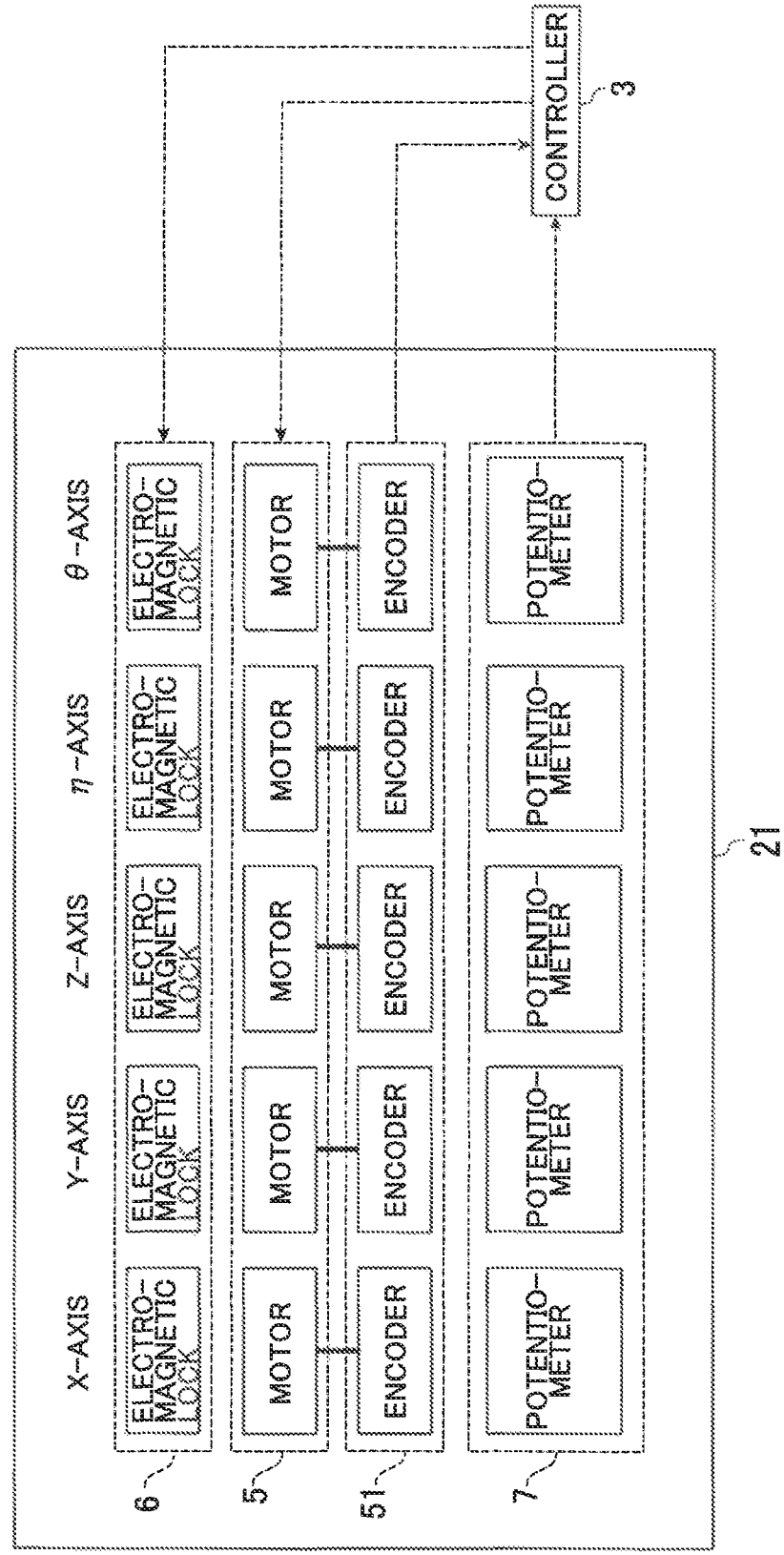
FIG. 5 is a block diagram showing the internal configuration of a moving body support and connection to a controller of the X-ray imaging apparatus according to the embodiment of the present invention.

As shown in FIG. 5, the moving body support 21 includes encoders 51 provided in the motors 5 for the respective axes, the locking mechanism 6, and the position detector 7.

The encoders 51 respectively detect the relative position of the moving body 1 in axial directions. Based on output signals of the encoders 51, it is possible to obtain the current position (the positions in the X, Y, and Z directions and the rotation angles in the η and θ directions) of the X-ray tube 11 of the moving body 1. The output signals of the encoders 51 are sent to the controller 3, and are used as positional information to control movement of the moving body 1.

The locking mechanism 6 switches between the unlocked state (a state in which the movement is permitted) and the locked state (a state in which the movement is prohibited) of the moving body 1 in each of the plurality of directions under control of the controller 3.

The position detector 7 includes potentiometers provided for the respective axes. Furthermore, the position detector 7 detects the absolute position of the moving body 1 by electrically outputting the length of a wire that has been pulled out by movement of the moving body 1. The output signals of the potentiometers are sent to the controller 3, and are used as positional information for control of movement of the moving body 1 such as power assist control. Information about the height position of the moving body 1 is detected by the potentiometer provided for the Z-axis.

The guide 22 is provided on the ceiling of the imaging room 101, as shown in FIG. 1. The guide 22 includes the plurality of rails and supports the moving body support 21 in such a manner that the moving body support 21 can be translated in the X direction and the Y direction. With these configurations, the moving body support 21 supports the moving body 1 in such a manner that the moving body 1 is movable in the X direction and the Y direction (horizontal direction) along the guide 22.

Specifically, as shown in FIG. 3, the guide 22 includes a fixed rail 221 fixed to the ceiling surface and movable rails 222. The fixed rail 221 and the movable rails 222 are examples of a "plurality of rails" in the claims. The fixed rail 221 extends linearly in the X direction. The movable rails 222 are attached to the fixed rail 221 in such a manner as to be movable in the X direction. The movable rails 222 extend linearly in the Y direction. The base 212 of the support rod 211 is attached to the movable rails 222 in such a manner as to be movable in the Y direction.

(Locking Mechanism)

As shown in FIG. 5, the locking mechanism 6 is provided inside the moving body support 21. The locking mechanism 6 locks movement of the moving mechanism 2 (moving body 1) corresponding to each of the plurality of directions.

Specifically, a plurality of electromagnetic locks (electromagnetic brakes) are provided as the locking mechanism 6. The locking mechanism 6 may be a hydraulic or mechanical brake, for example. The electromagnetic locks are configured to releasably lock movement of the moving body 1 in the plurality of directions, respectively.

The electromagnetic locks are respectively provided for the plurality of directions including the X, Y, Z, η, and θ directions. The electromagnetic locks can switch between locking and unlocking in the X, Y, Z, η, and θ directions, respectively. Thus, the locking mechanism 6 can switch between the unlocked state (a state of permitting the movement) of the moving body 1 in each of the plurality of directions and the locked state (a state of prohibiting the movement) of the moving body 1 in each of the plurality of directions.

The locking mechanism 6 is constantly maintained in the state (locking state) of prohibiting movement of the moving body 1 in each of the plurality of directions. Then, the locking mechanism 6 is individually switched to the state (unlocking state) of permitting movement of the moving body 1 in a direction determined by the controller 3. The operation of each electromagnetic lock is controlled by the controller 3.

Switching between the locking state and the unlocking state is performed by input operations of the buttons 13. The moving body 1 is provided with the plurality of buttons 13 for respectively switching between the locking state and the unlocking state in the plurality of directions (X, Y, Z, η, and θ).

The controller 3 can perform control to determine a direction in which movement of the moving body 1 is permitted based on the input operation of each button 13. The controller 3 is configured to perform control to individually switch the direction in which the movement is permitted based on a direction corresponding to the button 13 on which the input operation has been performed.

A multiple direction release mode in which multiple electromagnetic locks are unlocked and movement of the moving body 1 in multiple directions is permitted and a free mode in which movement of the moving body 1 in all directions is permitted may be provided. In such a case, on the moving body 1, a multiple direction release mode button (not shown) and a free mode button (not shown) may be separately provided as mode switching buttons.

When receiving an input operation of the multiple direction release mode button (or the free mode button), the controller 3 starts control to switch the multiple electromagnetic locks (or all the electromagnetic locks) to the unlocking state. In this case, the operator holds the grip 14 and can freely move the moving body 1 in the multiple directions (or all the directions).

When starting to control the multiple direction release mode (or the free mode), the controller 3 switches the electromagnetic locks to a state of prohibiting the movement in all of the plurality of directions based on a setting cancellation operation of the operator or a passage of time after permission of the movement in all of the plurality of directions. The setting cancellation operation of the operator includes inputting the multiple direction release mode button (or the free mode button) once to switch to the multiple direction release mode (or the free mode) and then inputting the multiple direction release mode button (or the free mode button) again, and inputting a dedicated cancel button (not shown), for example.

(Assisting Means)

Assisting means configured to provide assist when the moving body 1 is manually moved is now described with reference to FIG. 5.

The moving body support 21 (base 212) includes a motor 5 for an X-axis and a transmission mechanism for the X-axis (not shown). The transmission mechanism for the X-axis includes a belt-pulley mechanism, for example. When the motor 5 for the X-axis is driven to rotate, an assisting force is applied in the X direction to a pair of movable rails 222 (moving body 1).

The moving body support 21 (base 212) includes a motor 5 for a Y-axis and a transmission mechanism for the Y-axis (not shown). The transmission mechanism for the Y-axis includes a belt-pulley mechanism, for example, similarly to the transmission mechanism for the X-axis. When the motor 5 for the Y-axis is driven to rotate, an assisting force is applied in the Y direction to the support rod 211 (moving body 1).

The moving body support 21 (base 212) includes a motor 5 for the Z-axis and a transmission mechanism for he Z-axis (not shown). The transmission mechanism for the Z-axis is a winding mechanism including a wire (not shown) connected to the rotary holder 213 at the lower end of the support rod 211, for example. When the motor 5 for the Z-axis is driven to wind up the wire, an assisting force is applied in the Z direction to the rotary holder 213 (moving body 1).

The moving body support 21 (support rod 211) includes a motor 5 for a η-axis that rotationally drives the rotary holder 213 about the Z-axis. It is not necessary to directly connect the motor 5 for the η-axis to the rotary holder 213, and a transmission mechanism such as a reduction gear may be provided. The motor 5 for the η-axis applies an assisting force in the η direction to the rotary holder 213 (moving body 1).

The moving body support 21 (support rod 211) includes a motor 5 for a θ-axis that rotationally drives the moving body 1 about the R-axis. It is not necessary to directly connect the motor 5 for the θ-axis to the moving body 1, and a transmission mechanism such as a reduction gear may be provided. The motor 5 for the θ-axis applies an assisting force in the θ direction to the moving body 1.

The encoders 51 are respectively connected to the motors (for the X-axis, Y-axis, Z-axis, η-axis, and θ-axis). The operation of each of the motors (for the X-axis, Y-axis, Z-axis, η-axis, and θ-axis) is controlled by the controller 3. The controller 3 individually controls the motor 5 (for the X-axis, Y-axis, Z-axis, η-axis, or θ-axis) corresponding to a direction in which an assisting force is applied to be driven so as to generate an assisting force in the moving direction of the moving body 1.

(Power Assist Control)

The controller 3 performs control to change the amount of assist to be provided to the moving body 1 by the motors 5 according to the height position of the moving body 1 when the moving body 1 is manually moved.

The controller 3 also changes the amount of assist in the horizontal direction provided to the moving body 1 by the motors 5 according to the height position of the moving body 1 when the moving body 1 is manually moved.

Furthermore, the controller 3 changes the amount of assist provided to the moving body 1 by the motors 5 based on the height position detected by the position detector 7 when the moving body 1 is manually moved.

Moreover, the controller 3 changes the amount of assist in the horizontal direction along the plurality of rails (221, 222) provided to the moving body 1 by the motors 5 according to the height position of the moving body 1 when the moving body 1 is manually moved.

Specifically, the controller 3 is configured or programmed to control generated torques of the motors 5 based on the height position detected and acquired by the position detector 7 and an operating force detected by the force sensor 12 and to perform control to power-assist in moving the moving body 1 when the operator manually moves the moving body 1.

First, the controller 3 controls the potentiometer (position detector 7) provided for the Z-axis to detect and acquire the height position of the moving body 1 as needed. The potentiometers detect the absolute position of the moving body 1 by electrically outputting the length of the wire that has been pulled out by movement of the moving body 1. Then, when the operator unlocks the locking mechanism 6, holds the grip 14, and applies a force in the moving direction so as to move the moving body 1, the controller 3 controls the force sensor 12 to detect and acquire the operating force. The controller 3 corrects the influence of the weight and pose of the moving body 1 on the detected operating force to convert the detected operating force into operating forces in the respective directions. Then, the controller 3 controls the torques of the motors 5 provided for the respective axes so as to generate assisting forces according to the height position of the moving body 1 detected by the potentiometer (position detector 7) provided for the Z-axis, obtained by multiplying the converted operating forces by assist ratios.

For example, the controller 3 controls the torques of the motors 5, which are provided for the respective axes, of the moving body support 21 so as to generate the assisting forces according to the height position of the moving body 1, obtained by multiplying the converted operating forces by the assist ratios, as in an expression (1):

$$Ma = f_h - F_r + \alpha f_h \quad (1)$$

where M represents the mass of a moving portion (the moving body 1 and portions of the moving mechanism 2 moving when the moving mechanism 2 moves along the respective axes), a represents an acceleration, $f_h$ represents an operating force applied to the moving body 1, $F_r$ represents a resistance force, and a represents a ratio of the amount of assist to the operating force. M is several hundred kg, for example. In addition, α is about 1.5 or more and 10 or less, for example.

In this embodiment, the controller 3 is configured or programmed to increase the amount of assist ($\alpha f_h$) provided to the moving body 1 when the height position of the moving body 1 is equal to or more than a predetermined height upon manual movement of the moving body 1.

Specifically, when the height of the moving body 1 is equal to or more than the predetermined height, the controller 3 increases the amount of assist as the height increases. For example, the amount of assist is linearly increased according to the height position (about 1.5 or more and 10 times or less). Control is performed in this manner such that when manually moving the moving body 1, the operator can operate the moving body 1 without a sudden change in operational feeling even with a change in the height position. Furthermore, when the height of the moving body 1 detected by the position detector 7 is less than the predetermined height, the controller 3 makes the amount of assist provided to the moving body 1 by the motors 5 constant (about 1.5 times) so as to prevent an excessive decrease in the amount of assist when the position of the moving body 1 is low. The predetermined height may be based on a height at which the operator can easily move the moving body 1. For example, it is a height calculated based on the height of the operator (such as a threshold based on the average height of the operator).

With this configuration, when the moving body 1 (X-ray tube 11) is manually moved, power assist control corresponding to the height position of the moving body 1 is performed. Thus, the torques of the motors 5 are controlled such that the amount of assist provided to the moving body 1 changes, and the moving body 1 is moved in the X and Y directions (horizontal direction) along the plurality of rails (221, 222) and the Z, η, and θ directions.

Advantages of this Embodiment

According to this embodiment, the following advantages are obtained.

According to this embodiment, when the moving body 1 is manually moved, the controller 3 performs control to change the amount of assist to be provided to the moving body 1 by the drive (motors 5) according to the height position of the moving body 1. Accordingly, the amount of assist is increased when the height position of the moving body 1 is high such that feeling heavy in moving the moving body 1 can be significantly reduced or prevented even when the height position of the moving body 1 is high. Consequently, it is possible to significantly reduce or prevent a decrease in operability depending on the height position of at least one of the X-ray tube 11 and the X-ray detector 10 when at least one of the X-ray tube 11 and the X-ray detector 10 is manually moved.

According to this embodiment, the controller 3 is configured or programmed to increase the amount of assist provided to the moving body 1 by the drive (motors 5) when the height position of the moving body 1 is equal to or more than the predetermined height upon manual movement of the moving body 1. Accordingly, when the moving body 1 is at a high position, the amount of assist is increased, and thus even when the moving body 1 is at a high position, the moving body 1 can be easily moved manually.

According to this embodiment, the controller 3 is configured or programmed to make the amount of assist provided to the moving body 1 by the drive (motors 5) constant when the height position of the moving body 1 is less than the predetermined height and the moving body 1 is manually moved, and to increase the amount of assist as the height of the moving body 1 increases when the height position of the moving body 1 is equal to or more than the predetermined height and the moving body 1 is manually moved. Accordingly, when the height position of the moving body 1 is at a low position at which it is relatively easy for the operator to apply a force for moving the moving body 1, a change in the amount of assist can be significantly reduced or prevented. Thus, it is possible to significantly reduce or prevent a variation in operability depending on the height position at the low position at which it is relatively easy for the operator to move the moving body 1, and thus a decrease in operability can be significantly reduced or prevented.

According to this embodiment, the controller 3 is configured or programmed to change the amount of assist in the horizontal direction to be provided to the moving body 1 by the drive (motors 5) according to the height position of the moving body 1 when the moving body 1 is manually moved. Accordingly, it is possible to effectively significantly reduce or prevent a decrease in operability depending on the height position when the operator moves the moving body 1 in the horizontal direction in which a movement distance is larger than that in the vertical direction.

According to this embodiment, the drive includes the motors 5, and the controller 3 is configured or programmed to control the generated torques of the motors 5 so as to change the amount of assist to be provided to the moving body 1 by the motors 5 according to the height position of the moving body 1 when the moving body 1 is manually moved. Accordingly, the torques (drive forces) of the motors 5 are controlled such that the operating forces can be assisted. Therefore, the operating forces are assisted by direct forces (torques), and thus it is possible to perform good power assist with no sense of strangeness. In this respect as well, a decrease in operability can be significantly reduced or prevented.

According to this embodiment, the position detector 7 configured to detect the height position of the moving body 1 is further provided, and the controller 3 is configured or programmed to change the amount of assist to be provided to the moving body 1 by the drive based on the height position detected by the position detector 7 when the moving body 1 is manually moved. Accordingly, the amount of assist can be easily changed according to the height position detected by the position detector 7.

According to this embodiment, the moving mechanism 2 is further provided to support the moving body 1 in such a manner that the moving body 1 is movable in the predetermined directions, the moving mechanism 2 includes the plurality of rails provided in the horizontal direction, and the controller 3 is configured or programmed to change the amount of assist in the horizontal direction along the plurality of rails (the fixed rail 221 and the movable rails 222) to be provided to the moving body 1 by the motors 5 according to the height position of the moving body 1 when the moving body 1 is manually moved. Accordingly, even when the moving body 1 and the moving body support 21 are heavy, the moving body 1 and the moving body support 21 can be moved along the rails of the guide 22, and thus the operator can easily move the moving body 1 and the moving body support 21 also when manually moving the moving body 1.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the X-ray tube 11 is provided on the moving body 1 in the aforementioned embodiment, the present invention is not limited to this. In the present invention, the X-ray detector or both the X-ray tube and the X-ray detector may alternatively be provided on the moving body. Therefore, the present invention may be applied to an X-ray imaging apparatus in which an X-ray detector is provided on a moving body and is manually moved as in a proximate fluoroscopic table, or a C-arm type X-ray imaging apparatus in which both an X-ray tube and an X-ray detector are provided on a moving body and are manually moved.

While the amount of assist to be provided is increased when the height position of the moving body 1 is equal to or more than the predetermined height in the aforementioned embodiment, the present invention is not limited to this. In the present invention, the amount of assist to be provided may alternatively be increased when the height position of the moving body is less than the predetermined height.

While when the height position of the moving body 1 is less than the predetermined height and the moving body 1 is manually moved, the amount of assist to be provided is constant, and when the height position is equal to or more than the predetermined height and the moving body 1 is manually moved, the amount of assist to be provided is linearly increased according to the height position in the aforementioned embodiment, the present invention is not limited to this. In the present invention, even when the height position is less than the predetermined height, the amount of assist may not be constant, but may be changed linearly, for example. Alternatively, the predetermined height itself may not be provided. Alternatively, the amount of assist may not be changed linearly, but may be changed in a stepwise fashion or without monotonous increase, for example.

While the buttons 13 are physical buttons in the aforementioned embodiment, the present invention is not limited to this. In the present invention, the buttons may alternatively be buttons displayed on the touch panel.

While the controller 3 is disposed (provided) outside the imaging room 101 in the aforementioned embodiment, the present invention is not limited to this. In the present invention, the controller may alternatively be disposed inside the imaging room, or may alternatively be built in the moving body or the moving mechanism.

While the input device of the X-ray imaging apparatus 100 is the remote control 4 in the aforementioned embodiment, the present invention is not limited to this. In the present invention, the input device may alternatively be an input device such as a mouse or a keyboard.

While the controller 3 performs control to change the amount of assist based on the height position and the operating force in the aforementioned embodiment, the present invention is not limited to this. In the present invention, the controller may alternatively perform control to change the amount of assist based on another element (such as the speed of the moving body) in addition to the height position and the operating force.

While the amount of assist is changed by controlling the generated torques of the motors 5 (drive) in the aforementioned embodiment, the present invention is not limited to this. In the present invention, the amount of assist may alternatively be changed by controlling the rotation speeds of the motors.

While the position detector 7 is configured to detect the height position in the aforementioned embodiment, the present invention is not limited to this. In the present invention, for example, the operator may alternatively manually input height information using the touch panel or the like, and the controller may alternatively control the amount of assist based on the input height information.

While the position detector 7 includes the potentiometers in the aforementioned embodiment, the present invention is not limited to this. In the present invention, the position detector may alternatively include encoders or laser distance measurement sensors, for example.

What is claimed is:
1. An X-ray imaging apparatus comprising:
an X-ray tube configured to irradiate a subject with X-rays;

an X-ray detector configured to detect the X-rays transmitted through the subject;

a moving body configured to support at least one of the X-ray tube and the X-ray detector in such a manner that at least the one of the X-ray tube and the X-ray detector is movable in a predetermined direction;

a drive configured to provide an amount of assist for moving the moving body in the predetermined direction; and a controller configured or programmed to perform control to change the amount of assist to be provided to the moving body by the drive according to a height position of the moving body when the moving body is manually moved.

2. The X-ray imaging apparatus according to claim 1, wherein the controller is configured or programmed to increase the amount of assist provided to the moving body by the drive when the height position of the moving body is equal to or more than a predetermined height upon manual movement of the moving body.

3. The X-ray imaging apparatus according to claim 1, wherein the controller is configured or programmed to make the amount of assist provided to the moving body by the drive constant when the height position of the moving body is less than a predetermined height and the moving body is manually moved, and to increase the amount of assist as a height of the moving body increases when the height position of the moving body is equal to or more than the predetermined height and the moving body is manually moved.

4. The X-ray imaging apparatus according to claim 1, wherein the controller is configured or programmed to change the amount of assist in a horizontal direction to be provided to the moving body by the drive according to the height position of the moving body when the moving body is manually moved.

5. The X-ray imaging apparatus according to claim 1, wherein
the drive includes a motor; and
the controller is configured or programmed to control a generated torque of the motor so as to change the amount of assist to be provided to the moving body by the drive according to the height position of the moving body when the moving body is manually moved.

6. The X-ray imaging apparatus according to claim 1, further comprising a position detector configured to detect the height position of the moving body; wherein
the controller is configured or programmed to change the amount of assist to be provided to the moving body by the drive based on the height position detected by the position detector when the moving body is manually moved.

7. The X-ray imaging apparatus according to claim 1, further comprising a moving mechanism configured to support the moving body in such a manner that the moving body is movable in the predetermined direction; wherein
the moving mechanism includes a plurality of rails provided in a horizontal direction; and
the controller is configured or programmed to change the amount of assist in the horizontal direction along the plurality of rails to be provided to the moving body by the drive according to the height position of the moving body when the moving body is manually moved.

* * * * *